US00PP35728P2

(12) United States Plant Patent
Reisch et al.

(10) Patent No.: US PP35,728 P2
(45) Date of Patent: Apr. 9, 2024

(54) GRAPEVINE PLANT NAMED 'ARAVELLE'

(50) Latin Name: ***Vitis* spp., interspecific hybrid**
Varietal Denomination: ARAVELLE

(71) Applicant: Cornell University, Ithaca, NY (US)

(72) Inventors: Bruce I. Reisch, Geneva, NY (US); R. Stephen Luce, Ovid, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 18/189,085

(22) Filed: Mar. 23, 2023

(51) Int. Cl.
*A01H 5/08* (2018.01)
*A01H 6/88* (2018.01)

(52) U.S. Cl.
USPC ..... Plt./207
CPC ..... *A01H 6/88* (2018.05)

(58) Field of Classification Search
USPC ..... Plt./207
CPC ..... A01H 6/88; A01H 5/08
See application file for complete search history.

*Primary Examiner* — Keith O. Robinson
(74) *Attorney, Agent, or Firm* — MORRISON & FOERSTER LLP

(57) ABSTRACT

The invention is a new and distinct variety of grapevine plant named 'ARAVELLE', which is characterized by its adaptability to the Finger Lakes grape production region of New York and similar regions; fruit suitable for production of wines; moderate resistance to downy and powdery mildews; and resistance to *Botrytis* bunch rot.

3 Drawing Sheets

Genus and species: *Vitis* spp., interspecific hybrid.
Variety denomination: 'ARAVELLE'.

BACKGROUND OF THE INVENTION

Grapes are produced on deciduous lianas of the botanical genus *Vitis*. Grapes can be consumed as fresh fruit (table grapes) or they can be processed into wine, jam, juice, jelly, grape seed extract, raisins, vinegar, and grape seed oil. Grapes may also be dried to produce raisins. Grape clusters can include from about 15 to greater than 300 berries, and fruit color can vary greatly from crimson, black, or dark blue, to yellow, green, orange, or pink in color. Anthocyanins and other pigments are responsible for the varying shades of purple in red wines. Berry shapes may vary from round or ellipsoid to oval or falcoid.

Most grapes worldwide are produced by cultivars of *Vitis vinifera*, the European grapevine that is native to the Mediterranean and Central Asia. Some fruit are also produced from additional species, and many species have been hybridized with *V. vinifera* to create a range of wine, juice, raisin and table grapes, as well as rootstock vines.

White wine grapes are those lacking anthocyanin pigmentation in the fruit such that the wines produced have a clear to golden, non-opaque appearance. They are usually higher in titratable acidity than are table grapes grown for fresh consumption. Typical white wine grape cultivars include 'Chardonnay' (unpatented), 'Sauvignon blanc' (unpatented), 'Pinot gris' (unpatented), 'White Riesling' (unpatented), 'Seyval blanc' (unpatented) and many others.

Important characteristics of white wine grapes in New York and elsewhere include productivity; low temperature tolerance; resistance to foliar and fruit diseases; suitable balance of sugar, acidity and pH; as well as the ability to make wines that are pleasing to consumers. The present invention is a new grapevine variety that is well-adapted to summer and winter conditions in the Finger Lakes region of New York, and similar areas; is productive under such conditions; moderately resistant to grapevine powdery and downy mildew; and much more resistant to Botrytis fruit rot than is its parent, 'White Riesling'. In addition, the wine quality is very high, similar in aroma and flavor to wines made from 'White Riesling'.

SUMMARY OF THE INVENTION

The present invention relates to a new and distinct grape cultivar named 'ARAVELLE', which was discovered in 1985, and resulted from controlled pollinations that took place in June, 1981, at a research farm in Geneva, New York. The male parent was the well-known European wine grape, 'White Riesling' (unpatented), of the species *Vitis vinifera*. The female parent was 'Cayuga White' (unpatented; Einset, J. and W. B. Robinson. 1972. 'Cayuga White', the first of a Finger Lakes series of wine grapes for New York. N.Y. Food & Life Sci Bul. 22), which was the first grape developed specifically for wine production in Geneva, New York. 'Cayuga White' was developed from a seedling arising from the hybridization of 'Seyval blanc' (unpatented) and 'Schuyler' (unpatented), both grape varieties having multiple *Vitis* species in their ancestries.

I. Breeding History

The original cross was designed in 1981 and made that year (June 1981) by emasculating the female vine prior to flowering, and applying pollen of the male vine to the bagged and protected pistils of the female parent. Seed were then germinated in a greenhouse in spring of 1982 and this family of grapevines was grown in an irrigated field nursery that summer.

All work to develop this variety took place at a research farm in Geneva, New York, and in nearby farms. Test plots were also grown at Fredonia, New York; Penn Yan, New York; and with University and grower cooperators. Cross pollination was followed by selection and asexual reproduction of an elite seedling noted for excellent wine quality, productivity and resistance to Botrytis bunch rot.

From the cross made in 1981, 457 seeds were produced and 145 seedling grapevines were germinated in a greenhouse beginning March, 1982, and grown in a nursery (June to October, 1982 and 1983) at a research farm in Geneva, New York. These seedlings were then planted in May, 1983, to a permanent vineyard site. The original vine of cultivar 'ARAVELLE' was planted on a research farm in Geneva, New York (vineyard 30, row 1 vine 38). The first fruit produced were observed in 1985 and, the vine was propagated by hardwood cuttings for further testing in spring 1990 based on outstanding wine results from the 1988 harvest. After hardening under field conditions in the 1990 nursery, vines were stored moist and cold (under 5° C.) until planting in the spring. Six vines were then planted in the research farm in Geneva, New York, Vineyard 33 Row 28 Vines 18-21 in 1991, and initially bore fruit in 1993, with sufficient quantities to harvest for wine trials in 1994.

II. Asexual Reproduction & Stability

The method of asexual reproduction was that vines were propagated initially from hardwood cuttings and later via bench grafting on rootstock 'Couderc 3309' ('C. 3309'; unpatented). Seedlings from the cross described above were first asexually propagated are a research farm in Geneva, New York.

Asexual reproduction of this new cultivar by hardwood cuttings as well as by grafting onto a commercial rootstock shows that the characteristics and distinctions come true to form and are established and transmitted through succeeding propagations.

III. Comparisons with Parental and Reference Varieties

The 'ARAVELLE' cultivar is distinguished from 'White Riesling' and 'Cayuga White' as follows: Clusters are moderate in weight (ca. 100 gm/cluster) and hardiness is suitable for USDA Zone 5. The fresh flavor of the fruit has notes of apricot and stone fruits and the wine is often likened to 'White Riesling'. Berries are smaller than those of 'Cayuga White' and similar in size to 'White Riesling', but the clusters are longer and looser than those of 'White Riesling'.

BRIEF DESCRIPTION OF THE DRAWINGS

New grapevine plant 'ARAVELLE' is illustrated by the accompanying photographs. The plant shown in the photographs is 11 years old. The colors of these illustrations may vary with lighting conditions and, therefore, color characteristics of this new cultivar should be determined with reference to the observations described herein, rather than from these illustrations alone.

DETAILED BOTANICAL DESCRIPTION

Figure 1:
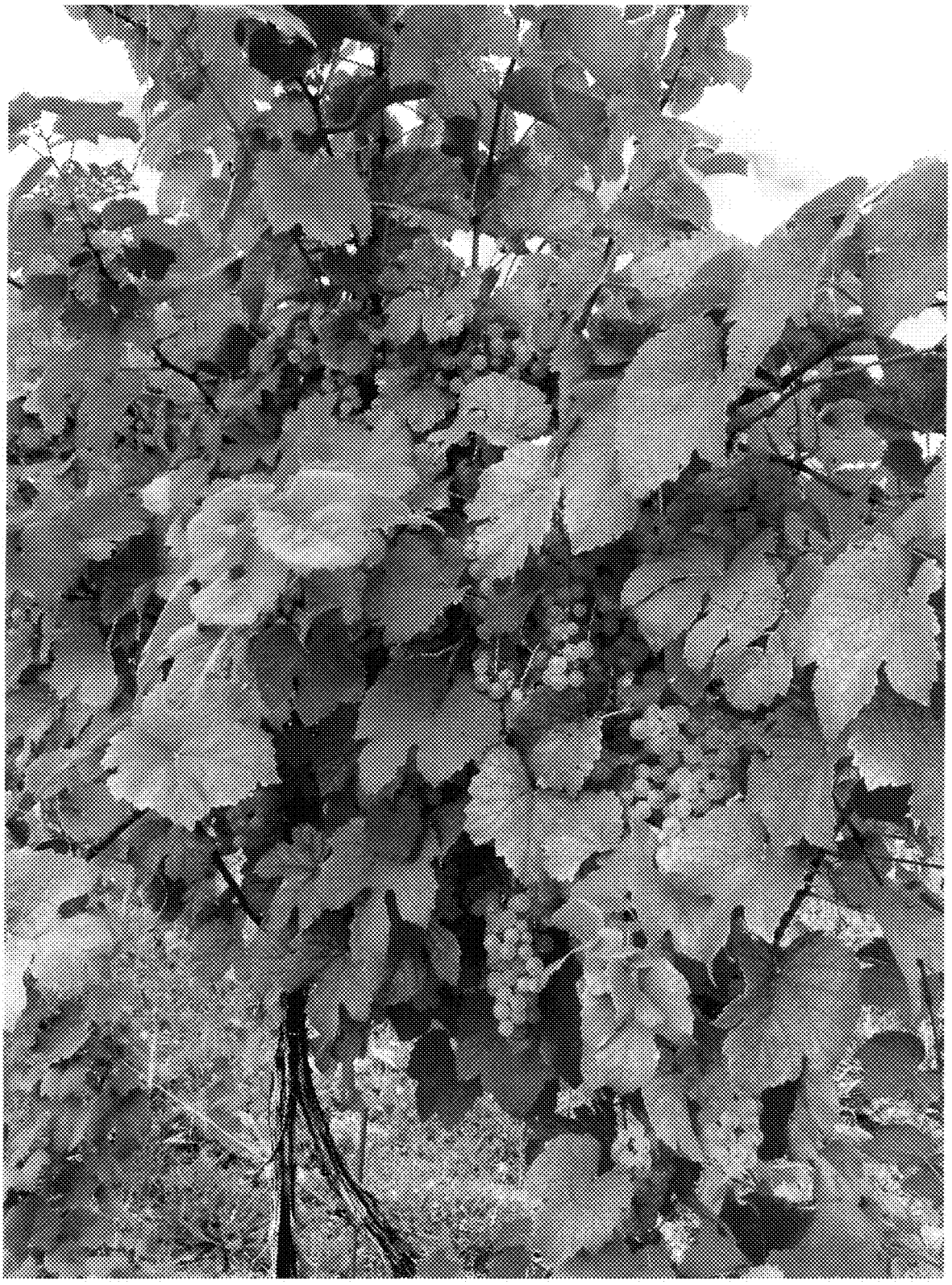
FIG. 1 illustrates a mature 'ARAVELLE' vine with fruit clusters.
Figure 2:
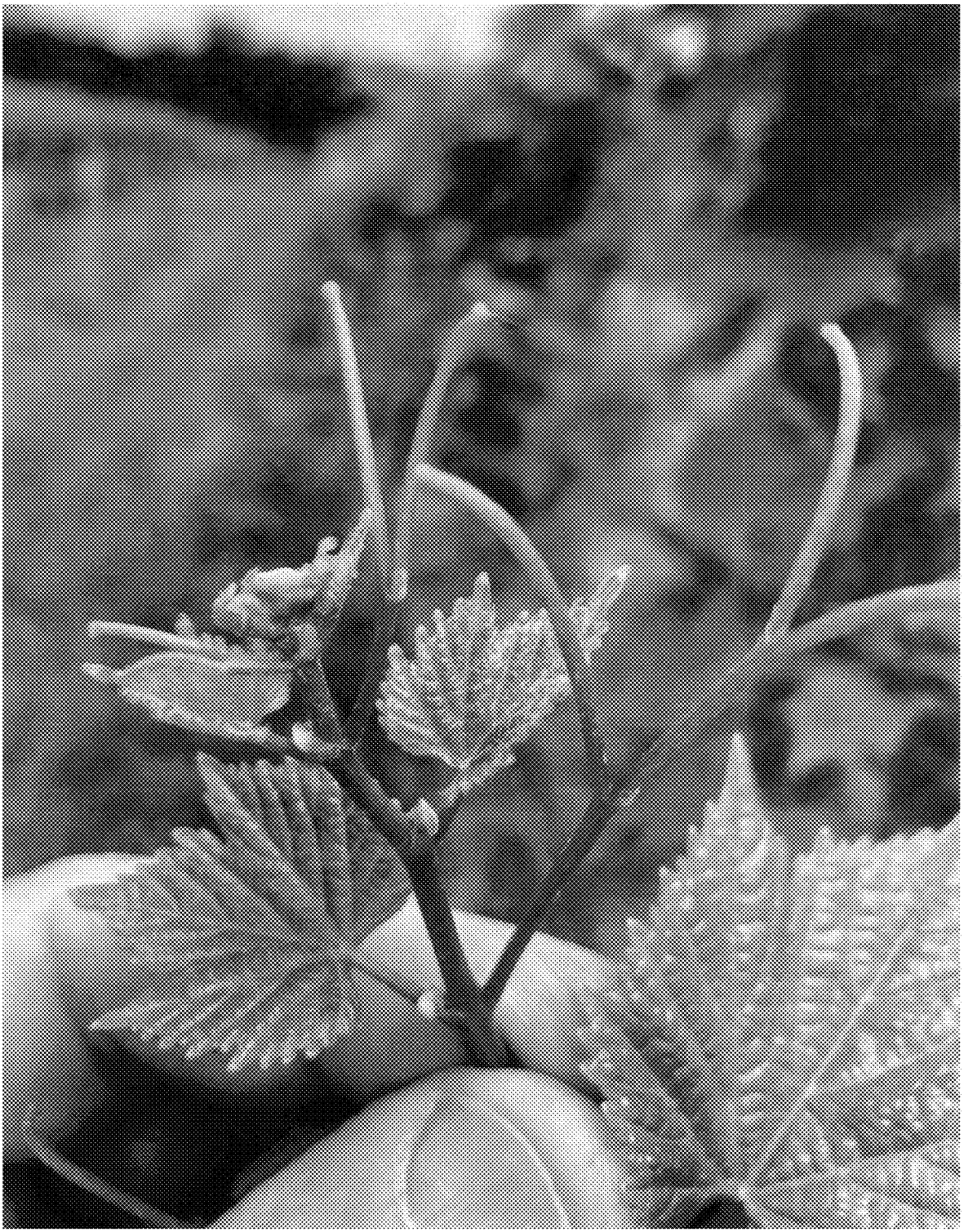
FIG. 2 illustrates a young shoot of 'ARAVELLE', and was taken in June 2021.
Figure 3:
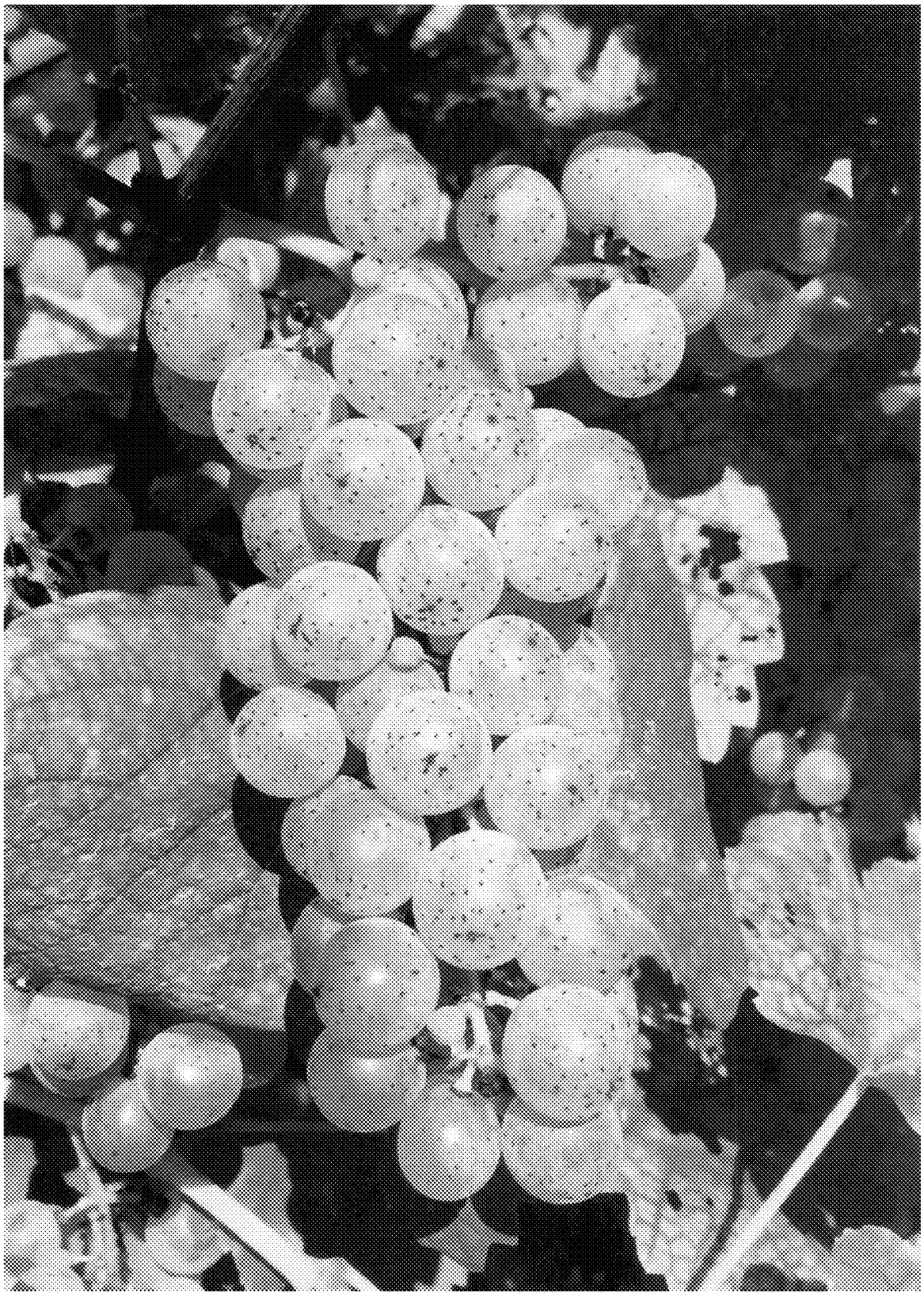
FIG. 3 illustrates a fruit cluster of 'ARAVELLE'.

The following detailed description of the 'ARAVELLE' grapevine plant is based on the originally identified plant, and asexually reproduced progeny grown on a research farm in Geneva, New York. The own-rooted vines described were planted in 1994, while the vines grafted on 'C. 3309' rootstock were planted in 1999. Vine, disease resistance, and fruit (only cluster weight and berry weight) data were obtained from these plants. Unless otherwise indicated, 11 year old vines in a separate planting were the source of the cane, leaf, flower, and further fruit (only peduncle, pedicel, brush, and seed fresh weight) data. Certain characteristics of this cultivar may change with changing environmental conditions (e.g., light, temperature, moisture, etc.), nutrient availability, or other factors. Quantified measurements are expressed as an average of measurements taken from a number of individual plants and plant parts of the new cultivar. The measurements of any individual plant, or any group of plants, of the new cultivar may vary from the stated average. Color descriptions and other terminology are used in accordance with their ordinary dictionary descriptions, unless the context clearly indicates otherwise. All major color code designations are by reference to The Royal Horticultural Society Colour Chart (R.H.S.), 2001 edition.

Vine:

*Size*.—Medium vine size as determined on grapevines growing on a three wire vertical trellis with the first wire set 86.4 cm (34 in) above the ground; the second wire at 127 cm (50 in) above the ground; and the third wire at 178 cm (70 in) above the ground. The vine was trained to produce a grapevine height of 191 cm (75 in) and a grapevine spread of 244 cm (96 in). Vine size as indicated by the weight of dormant prunings of cane-pruned grapevines was 0.54 kg (1.2 lbs.) for own-rooted vines (1996-2011) and 1.4 kg (3.0 lbs.) for vines grafted on 'C. 3309' rootstock (2001-2003).

*Productivity*.—Productive. Grafted vines produced 7.6 kg of fruit (2001-2003), while own rooted vines produced 5.6 kg (1996-2011) when spaced 8 ft. (244 cm) between vines and 9 ft. (274 cm) between rows.

*Regularity of bearing*.—Regular. Annual pruning of canes and/or 4-6 bud spurs is required for reliable production.

Canes:

*Diameter of mature canes*.—7.1 mm (12 year old vines grafted on 'C. 3309' rootstock; canes from primary buds measured between nodes 3 to 5). Semi-trailing in growth habit.

*Diameter of internode midpoint above node* 4.—5.9 mm own rooted and 7.9 mm grafted.

*Internode length*.—Base, between nodes 1 and 2: 3.47 cm own rooted and 3.20 cm grafted. Between nodes 2 and 3: 4.53 cm own rooted and 4.87 cm grafted. Between nodes 3 and 4: 5.24 cm own rooted and 5.81 cm grafted. Between nodes 4 and 5: 5.68 cm own rooted and 6.07 cm grafted.

*Surface texture*.—Smooth.

*Color of mature cane*.—Brown with thin darker longitudinal stripes. The stripes are Brown (Fan 4, RHS 200C), and the background ranges approximately from Grey-Brown (Fan 4, RHS 199C) to Brown (Fan 4, RHS 200D).

*Color of buds*.—Approximately Greyed-Purple (Fan 4, RHS N186C).

*Date of bud break*.—In 2021 at a vineyard in Dresden, New York, budbreak took place on May 5 and 6 for 'ARAVELLE', the same time as its parents, 'Cayuga White' and 'White Riesling'. On May 6, 'Vidal blanc' (unpatented) had swollen buds but none of the leaves had separated from the bud.

*Young shoots*.—Surface texture: Smooth texture, not hairy. Youngest leaves at the tip have wooly pubescent hairs. Young shoots are smooth. Color: Yellow-Green (Fan 3, RHS 144C to 144B; older shoots are RHS 144A).

*Stem of shoot tip color*.—Yellow-Green (Fan 3, RHS 144A).

*Color of youngest leaf, not expanded*.—Upper surface Green (Fan 3 RHS 144D) to Greyed Red (Fan 4, RHS 178C). Lower surface: Slight whitish pubescence, Yellow-Green (Fan 3, RHS N145C).

*Shape of shoot*.—Open, straight to slightly curved.

*Form of shoot tip*.—Open, flattened leaves folded at the tip.

*Tendril*.—Shape: Both bifurcated and trifurcated, and curled on distal end. Surface texture: Smooth. Color of immature growth: Yellow green (Fan 3, RHS N144A).

Disease resistance: Grown under conditions where a fungicide program was used for medium level control of the prevalent diseases, symptoms of downy mildew were occasionally observed, and leaf powdery mildew was observed one month after the final fungicide application. Vines of cultivar 'ARAVELLE' are categorized as being moderately resistant to downy mildew (*Plasmopara viticola*) and moderately resistant to foliar powdery mildew (*Erisyphe necator*).

Leaves:

*General size and type*.—Leaves medium, simple and alternate.

*Average length*.—11 cm.

*Average width*.—10.7 cm.

*Vein length and angles*.—The mid vein (L1) is 8.3 cm long. Vein L2 is 7.5 cm long, and vein L3 is 5.5 cm long. The angle between the mid vein L1 and L3 is 83.9 degrees and between L1 and the 1st vein off L3 is 120.4 degrees.

*Shape*.—Orbicular-reniform.

*Lobe number*.—Mostly 3.

*Adaxial surface*.—Slightly convex, and bullate.

*Abaxial surface*.—Nearly hairless or very sparse cobwebby hairs.

*Mature leaf*.—Color of adaxial surface: Green (Fan 3, RHS 138A). Color of abaxial surface: Green (Fan 3, RHS 138 B). Color of leaf vein: Yellow green (Fan 3, RHS 144D). Leaf vein thickness: 0.5 mm at center of leaf.

*Leaf margin*.—Teeth not prominent, with shape of teeth mostly convex, medium in size (not flat or narrow).

*Petiole sinus*.—Shape: Open lyre shaped. Size on mature leaf: 2-3 cm long and 2-4 cm wide at widest point.

*Anthocyanin, main veins*.—None.

*Petiole*.—Length: 5 cm. Diameter: 2.2 mm. Surface texture: Smooth but with very sparse short hairs. Color: Yellow green (Fan 3, RHS 144C).

*Shape of unfolded young leaf*.—Cuneiform 146-3-35.

*Petiole of young leaf color*.—Yellow green (Fan 3, RHS 144C) to Greyed red (Fan 4, RHS 178C).

Flowers:

*Unopened flower*.—Diameter: 1.6 mm. Length: 2.4 mm. Surface texture: Smooth.

*Date of bloom*.—Trace bloom Jun. 9, 2021 ('Cayuga White', June 8; 'Riesling', June 10).

*Date of* 50% *bloom*.—Jun. 11, 2021 ('Cayuga White', June 10; 'Riesling', June 13).

*Inflorescence*.—Panicle.

*Fragrance*.—Slightly aromatic.

*Cluster size*.—Pre-bloom cluster length: 12.7 cm (10 clusters on Jun. 9, 2021). Pre-bloom cluster width: 4.7 cm (10 clusters on Jun. 9, 2021). Pre-bloom cluster peduncle length: 2.9 cm (10 clusters on Jun. 9, 2021).

*Peduncle color*.—Yellow green (Fan 3, RHS 145C).

*Shape of cluster*.—Shouldered/conical, occasionally winged.

*Flower* (*calyptra*) *color*.—Yellow Green (Fan 3, RHS 144B).

*Stamens*.—Five (5) or six (6) per flower.

*Pistil*.—Well developed.

*Ovary color*.—Yellow Green (Fan 3, RHS 144C).

*Pollen*.—Normal. fertile. Abundant.

*Anther color*.—Greyed yellow (Fan 4, RHS 162D).

Fruit:

*Use*.—White wine grape,

*Maturity when described*.—Ripe for harvest approximately late September to early October, when grown in Geneva, New York.

*Cluster* (*bunch*) *weight on cane pruned vines*.—109 grams (0.24 lb., 2001-03) on grafted vines, and 109 grams (0.24 lb., 1996-2011) on own rooted vines.

*Cluster* (*bunch*) *length*.—15.6 cm (12 year old vines grafted on 'C. 3309' rootstock; measured at ripe stage).

*Cluster* (*bunch*) *width*.—8.1 cm (12 year old vines grafted on 'C. 3309' rootstock; measured at ripe stage; measured at widest point using basal clusters on primary shoots).

*Shape*.—Shouldered, occasionally winged.

*Density*.—Well-filled to compact.

*Clusters per shoot*.—2 clusters per primary shoot.

*Peduncle*.—Length: 3.2 cm on own-rooted vines. Diameter: 4.1 mm on own-rooted vines. Color: Yellow Green (Fan 3, RHS 145B), sometimes mixed/striped in the sun with Greyed-Purple (Fan 4, RHS 185C). Texture: Smooth, with very sparse short Greyed-Brown (Fan 4, RHS 199A to 199B) hairs (mostly seen on sun-exposed clusters).

*Pedicel*.—General: There is a strong attachment between the berry and the pedicel. Length: 7.2 mm on own-rooted vines. Diameter: 1.5 mm on own-rooted vines. Color: Green (Fan 3, RHS 145B to 145C).

*Brush*.—Length: 3.4 mm on own-rooted vines. Color: Yellow-Green (Fan 3, RHS 150C).

*Berry*.—Weight: Medium. Average of 1.54 gm/berry on grafted vines in 2002-03, and 1.59 gm/berry on own-rooted vines 1996-2010. Uniformity: Moderately uniform in size. Shape: Spherical. Size: 14.5 mm long and 15.3 mm wide on own-rooted vines. Color: With waxy bloom in place, Greyed yellow (Fan 4, RHS 161A). Bloom: Moderate. Surface Texture: Smooth with prominent lenticel dotting throughout the skin surface. Tendency to crack: Very slight, exacerbated by bird or insect damage. Flesh color: Yellow green (Fan 3, RHS 145C). Texture: Slightly firm, juicy. Flavor: Fruity, similar to 'Riesling'. Soluble solids: 19.6° Brix in 1996-2011. Titratable acidity: 10.3 g/L in in 1996-2011. pH: 2.97 in 1996-2011.

*Seeds*.—Well-formed.

*Seed counts and weights*.—2 to 4 seeds per berry (same for grafted and own-rooted vines).

*The fresh weight per seed in* 2021 *was* 39 *mg*.

*Ripening*.—Uniform.

What is claimed is:

1. A new and distinct variety of grapevine plant named 'ARAVELLE' as described and illustrated herein.

* * * * *